United States Patent
Rawat et al.

(10) Patent No.: US 8,440,844 B2
(45) Date of Patent: May 14, 2013

(54) PROCESS FOR THE PREPARATION OF β-AMINO ALCOHOL

(75) Inventors: Varun Rawat, Noida (IN); Pandurang Vilasrao Chouthaiwale, Pune (IN); Vilas Bhiku Chavan, Pune (IN); Gurunath Mallappa Suryavanshi, Pune (IN); Arumugam Sudalai, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/273,022

(22) Filed: Oct. 13, 2011

(65) Prior Publication Data

US 2012/0330031 A1 Dec. 27, 2012

(30) Foreign Application Priority Data

Jun. 21, 2011 (IN) .............................. 1749/DEL/2011

(51) Int. Cl.
*C07D 333/34* (2006.01)

(52) U.S. Cl.
USPC .......................................................... 549/65

(58) Field of Classification Search ...................... 549/65
See application file for complete search history.

(56) References Cited

U.S. PATENT DOCUMENTS 6,800,764 B2 * 10/2004 Kreft et al. ........................ 549/65

OTHER PUBLICATIONS

Vilaivan, T., et al. "Organocatalyzed Asymmetric α-Oxidation, α-Aminoxylation and α-Amination of Carbonyl Compounds." Molecules. vol. 15, (2010). pp. 917-958.*
Cho et al., "Application of optically active 1,2-diol monotosylates for synthesis of β-azido and β-amino alcohols with very high enantiomeric purity. Synthesis of enantiopure (R)-octopamine, (R)-tembamide and (R)-aegeline," *Tetrahedron Asymmetry*, 13(11):1209-1217, 2002.
Cordova et al., "The direct catalytic asymmetric α-aminooxylation reaction: Development of stereoselective routes to 1,2-diols and 1,2-amino alcohols and density functional calculations," *Chemistry*, 10(15):3673-3684, 2004.
He et al., "Regioselective and stereospecific azidation of 1,2- and 1,3-diols by azidotrimethylsilane via a mitsunobu reaction," *J. Org. Chem.*, 64(16):6049-6055, 1999.
Vilaivan et al., "Organocatalyzed asymmetric alpha oxidation, alpha aminooxylation and alpha amination of carbonyl compound," *Molecules*, 15:917-958, 2010.

* cited by examiner

*Primary Examiner* — Andrew D Kosar
*Assistant Examiner* — John S Kenyon
(74) *Attorney, Agent, or Firm* — Fulbright & Jaworski L.L.P.

(57) ABSTRACT

A high-yielding enantioselective synthesis of the bioactive (S)—N-(5-chlorothiophene-2-sulfonyl)-β,β-diethylalaniol (7.b.2), a Notch-1-sparing γ-secretase inhibitor metabolite (with $EC_{50}=28$ nM) effective in reduction of Aβ production in vivo, has been realized starting from readily available 3-pentanone. The key steps of the synthesis are proline-catalyzed α-aminooxylation and α-amination of aldehyde; the latter contributing an overall yield of 50-75% and 90-99% enantiomeric excess.

10 Claims, No Drawings

PROCESS FOR THE PREPARATION OF β-AMINO ALCOHOL

BACKGROUND OF THE INVENTION

1. Field of Invention

The present invention relates to a process for the preparation of chirally pure β-amino alcohol of general formula 1A. More particularly, the present invention relates to enantioselective synthesis of N-sulfonyl n-amino alcohols effective in reduction of β-amyloid (Aβ) production in vivo in the patient of Alzheimer's disease (AD). In particular, the present process involves proline catalyzed asymmetric α-aminooxylation and α-amination of aldehyde (4) to give the corresponding amino alcohol (9) a key intermediate for the preparation of compound of formula (1A) with an overall yield of 45.2% and 98% ee.

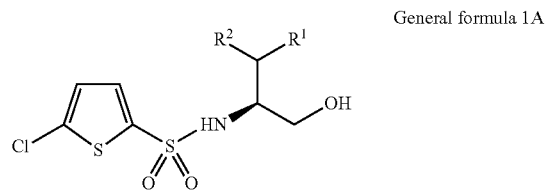

General formula 1A wherein, $R^1$ and $R^2$=ethyl, methyl, isopropyl or trifluoromethyl.

DESCRIPTION OF RELATED ART

Alzheimer's disease (AD) is a chronic, neurodegenerative disorder which is characterized by a loss of cognitive ability, severe behavioral abnormalities and ultimately death. A key event in the pathogenesis of AD is now believed to be the deposition of β-amyloid (Aβ) plaques on the outside of the nerve cells in areas of the brain that are produced by the proteolytic cleavage of amyloid precursor protein (APP) by β and γ-secretase A "β-amyloid cascade" hypothesis has emerged to account for various experimental facts including genetic variations related to the production and elimination of Aβ. Recent studies have further shown that neuritic plaques and neurofibriliary tangles are accepted pathological hallmarks of AD as confirmed at autopsy. γ-secretase inhibitors like BMS-299897, LY-450139 and MK-0752 have entered clinical trials. Recently (S)—N-(5-chlorothiophene-2-sulfonyl)-β,β-diethylalaninol a Notch-1-sparing γ-secretase inhibitor (with EC50=28 nM), has been found to be effective in reduction of Aβ production in vivo.

U.S. Pat. No. 6,800,764 titled 'Process for synthesis of chirally pure beta-amino-alcohols' discloses a process for preparing chirally pure S-enantiomers of alpha-amino acids from alkyl halide and alternatively reduction to β-amino alcohol as represented in the scheme below:

Scheme 2

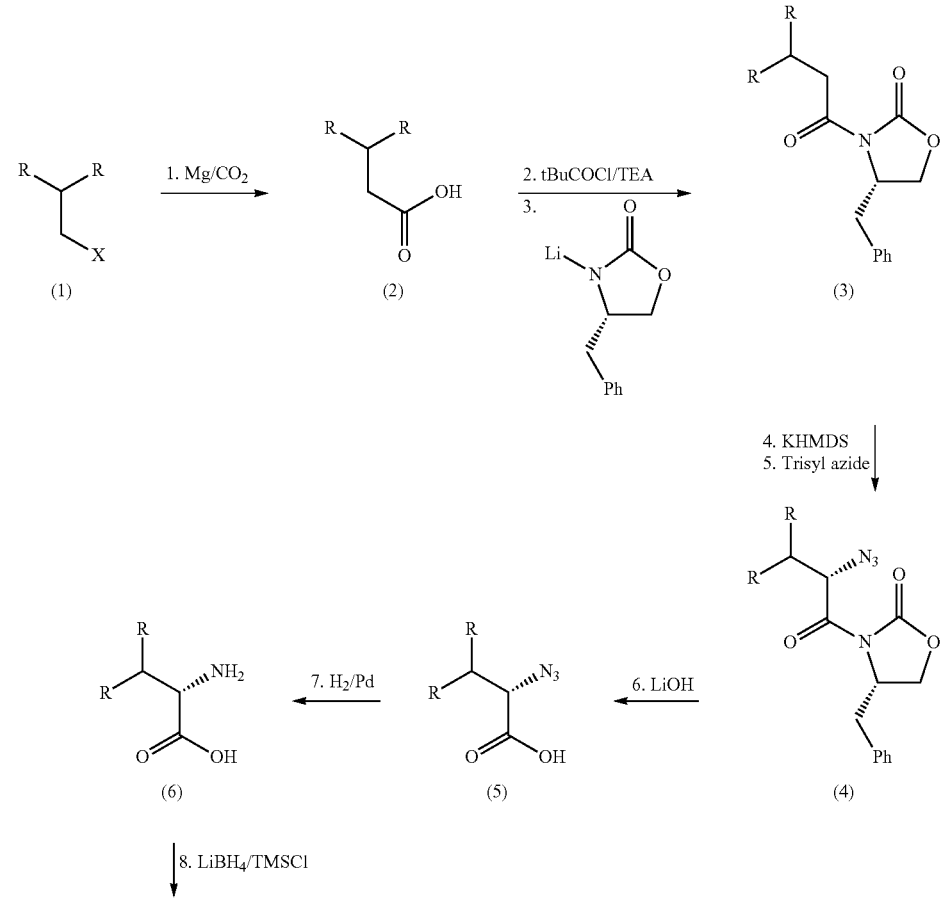

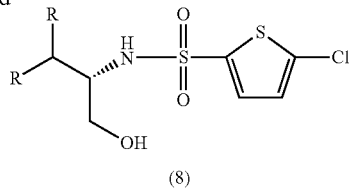

(7) → (8), reagent: 9. 5-Cl—Th-2-SO₂Cl

The process is however lengthy, involves use of costly reagents, uneconomical and time consuming.

Enantioselective organocatalysis has emerged as a powerful synthetic paradigm that is complementary to metal-catalyzed transformations and has accelerated the development of new methods to make diverse chiral molecules. The operational simplicity, ready availability of catalysts and low toxicity associated with organo catalysis makes it an attractive method to synthesize complex structures.

An amino acid proline which is present abundantly, is inexpensive and is available in both enantiomeric forms is now used as the most practical and versatile organo catalyst. Various prior arts discuss the use of proline catalyst for asymmetric alpha oxidation, alpha aminooxylation and alpha amination of carbonyl compound which are useful intermediates in the preparation of chirally pure beta-amino-alcohols.

Article titled "Organocatalyzed Asymmetric alpha Oxidation, alpha Aminooxylation and alpha Amination of carbonyl compound" by Tirayut Vilaivan et al. in Molecules 2010, 15, 917-958 having DOI:10.3390/molecules15020917 discloses alpha amination of simple alpha unbranched aldehydes with various azodicarboxylate esters under catalysis of L-proline (10 mol %) in presence of acetonitrile solvent at 0° C. to R.T. for 3 hours followed by reduction with $NaBH_4$ in situ to give the corresponding amino alcohols.

Proline Catalyzed α-Amination of Unbranched Aldehydes

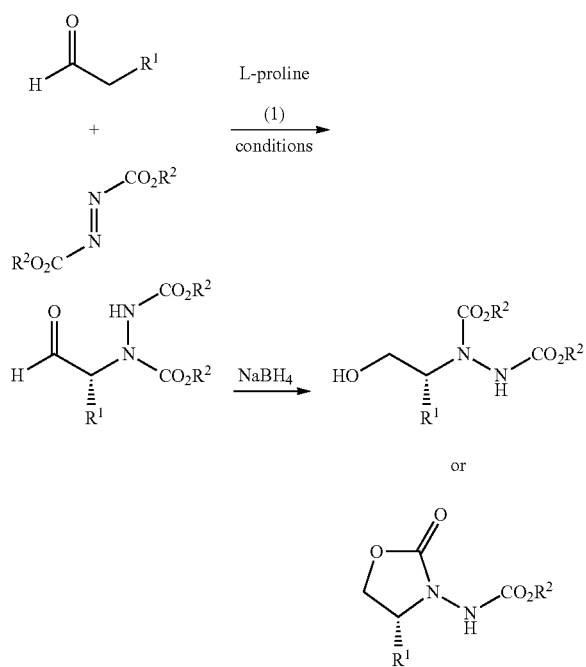

Article titled "The direct catalytic asymmetric α-aminooxylation reaction: Development of stereoselective routes to 1,2-diols and 1,2-amino alcohols and density functional calculations" by Cardova Armando et al. Journal title Chemistry ISSN 0947-6539. Source 2004, vol. 10, no. 15, pp. 3673-3684 [12 page(s) (article)] discloses proline-catalyzed direct asymmetric α-aminooxylation of ketones and aldehydes wherein unmodified ketones or aldehydes are reacted with nitrosobenzene in presence of proline as a catalyst. The direct preparation of enantiomerically pure epoxides and 1,2-amino alcohols are presented. The article also discloses direct catalytic α-oxidation for the stereoselective preparation of β-adrenoreceptor antagonists.

Article titled "Application of optically active 1,2-diol monotosylates for synthesis of β-azido and β-amino alcohols with very high enantiomeric purity. Synthesis of enantiopure (R)-octopamine, (R)-tembamide and (R)-aegeline in Tetrahedron: Asymmetry Volume 13. Issue 11, 21 Jun. 2002, Pages 1209-1217 having DOI 10.1016/S0957-4166(02)00322-1 discloses synthesis of enantiopure β-azido and β-amino alcohols, including biologically active substances such as (R)-octopamine, (R)-tembamide and (R)-aegeline from optically active 1,2-diol monotosylates.

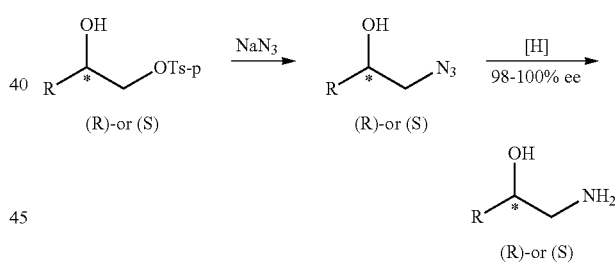

R = alkyl, aryl or 2-thienyl

Article titled "Regioselective and Stereospecific Azidation of 1,2- and 1,3-Diols by Azidotrimethylsilane via a Mitsunobu Reaction" in J. Org. Chem., 1999, 64 (16), pp 6049-6055 having DOI 10.1021/jo9906375 describes regio and stereospecific azidation reaction of 1,2 and 1,3-diols with azidotrimethylsilane ($Me_3SiN_3$) via a Mitsunobu reaction, further 1,2- and 1,3-diols, on reaction with triphenylphosphine, diisopropyl azodicarboxylate, and $Me_3SiN_3$ in dichloromethane gave regioselective azidation at C-2 and C-3, respectively.

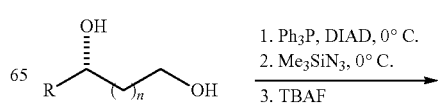

1. $Ph_3P$, DIAD, 0° C.
2. $Me_3SiN_3$, 0° C.
3. TBAF

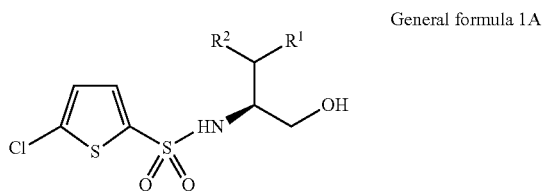

n = 0, 1

In its continued effort to work on proline-catalyzed synthesis of bioactive molecules, the present inventors have felt a need to invent a facile proline-catalyzed enantioselective synthesis of N-sulfonyl β-amino alcohols, whose activity makes it an attractive synthetic target.

SUMMARY OF THE INVENTION

The main objective of the present invention is to provide a process for the preparation of chirally pure β-amino alcohol of general formula 1A General formula 1A

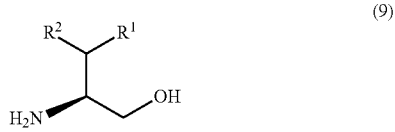

wherein, $R^1$ and $R^2$=ethyl, methyl, isopropyl or trifluoromethyl.

Another objective of the present invention is to provide a process for the preparation of chirally pure O-amino alcohol intermediate of formula (9)

formula (9)

(9)

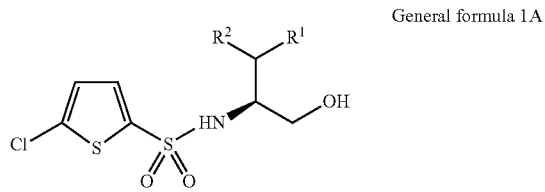

wherein, $R^1$ and $R^2$=ethyl, methyl, isopropyl or trifluoromethyl.

Another objective of the present invention to provide a process for the synthesis of N-sulfonyl β-amino alcohols of formula effective in reduction of β-amyloid (Aβ) production in vivo in the patient of Alzheimer's disease (AD).

Another objective of the present invention to prepare chirally pure beta-amino-alcohols useful as intermediates for the synthesis of bioactive molecule via proline catalyzed alpha aminooxylation and alpha amination of carbonyl compound.

Another objective of the invention is to synthesize N-sulfonyl β-amino alcohols in good yield, using inexpensive organo catalyst proline, wherein proline-catalyzed α-aminooxylation and α-amination reactions of carbonyl compounds constitute key steps for the introduction of chirality.

Accordingly, the present invention provides a process for the preparation of chirally pure β-amino alcohol of general formula 1A General formula 1A

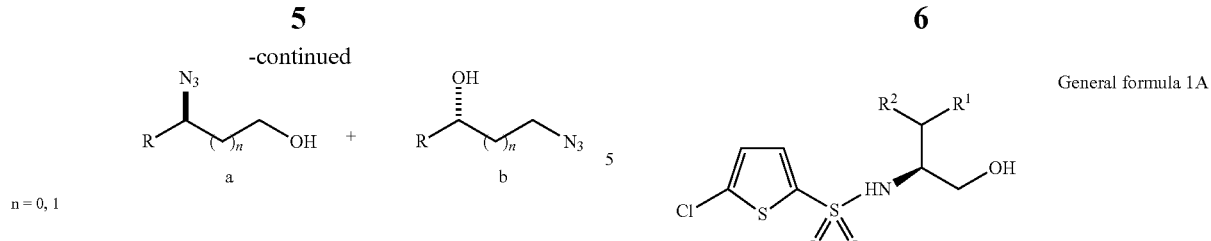

wherein $R^1$ and $R^2$=ethyl, methyl, isopropyl or trifluoromethyl, comprising the steps of:
  a. adding a ketone, triethyl phosphonoacetate, NaH and THF at temperature ranging between −10° C. to 10° C. for a period ranging between 5-15 h to obtain α,β-unsaturated ester;
  b. hydrogenating of α,β-unsaturated ester as obtained in step (a) with $H_2$ gas and in the presence of a catalyst for a period ranging between 12 h to 24 h at temperature ranging between 15° C. to 35° C. obtain saturated primary alcohol;
  c. oxidising alcohol as obtained in step (b) with IBX (o-iodoxy benzoic acid) in DMSO for a period ranging between 1 h to 4 h at temperature ranging between 10° C. to 35° C. to obtain aldehyde;
  d. α-aminating of aldehyde as obtained in step (c) using List's protocol for a period ranging between 2 h to 8 h at temperature ranging between −10° C. to 10° C. to obtain protected amino alcohol;
  e. hydrogenating of protected amino alcohol as obtained in step (d) with Raney nickel over hydrogen in presence of methanol and acetic acid for a period ranging between 22 h-48 h at temperature ranging between 15° C. to 35° C. to yield the intermediate alcohol;
  f. condensating of intermediate alcohol as obtained in step (e) with 5-chlorothiophene-2-sulfonyl chloride in the presence of triethylamine for a period ranging between 30 min to 6 h at temperature ranging between −10° C.-15° C. to yield β-amino alcohol of general formula 1A.

In one embodiment of the present invention, catalyst used in step (a) is selected from the group consisting of 10% Pd/C, lithium aluminum hydride, sodiumborohydride, rhodium catalyst.

In another embodiment of the present invention, ketone used in step (a) is 3-pentanone.

In another embodiment of the present invention, yield and enantiomeric excess of β-amino alcohol is the range of 50%-75% and 90%-99% respectively.

In another embodiment of the present invention, a process for the preparation of chirally pure β-amino alcohol of general formula 1A is provided General formula 1A wherein, $R^1$ and $R^2$=ethyl, methyl, isopropyl or trifluoromethyl, wherein the said process comprises the step of:
  a. adding a ketone, triethyl phosphonoacetate, NaH and THF at temperature ranging between −10° C. to 10° C. for a period ranging between 5-15 h to obtain α,β-unsaturated ester;
  b. hydrogenating of α,β-unsaturated ester as obtained in step (a) with $H_2$ gas and in the presence of a catalyst for a period ranging between 12 h to 24 h at temperature ranging between 15° C. to 35° C. obtain saturated primary alcohol;

c. oxidising alcohol as obtained in step (b) with IBX (o-iodoxy benzoic acid) in DMSO for a period ranging between 1 h to 4 h at temperature ranging between 10° C. to 35° C. to obtain aldehyde;

d. α-aminooxylating of aldehyde as obtained in step (c) in the presence of L-praline and PhNO (nitroso benzene) at temperature ranging between −30° C. to 0° C. for a period ranging between 15 h to 30 h to obtain crude α-aminooxy alcohol and subsequent reduction with $H_2$ gas and a catalyst at temperature ranging between 15° C. to 35° C. for a period ranging between 12 h to 35 h to furnish chiral diol;

e. protecting hydroxyl group in diol as obtained in step (d) with tert-Butyl dimethylsilyl chloride (TBSCl) in imidazole and $CH_2Cl_2$ to yield protected ether and further mesylation of protected ether to yield protected mesylate;

f. regioselective azidation of protected mesylate as obtained in step (e) with sodium azide in DMF at temperature ranging between 45° C.-70° C. for a period ranging between 20 h to 48 h to give protected azide;

g. reduction of protected azide as obtained in step (f) with $LiAlH_4$ in THF at temperature ranging between 40° C.-60° C. for a period ranging between 5 h to 20 h to yield the intermediate alcohol;

h. condensating of intermediate alcohol as obtained in step (d) with 5-chlorothiophene-2-sulfonyl chloride in the presence of Et3N to yield β-amino alcohol of general formula 1A.

In another embodiment of the present invention, catalyst used in step (a) is selected from the group consisting of 10% palladium on carbon catalyst, Raney nickel, rhodium, indium, Zn/HCl, sodium borohydride, lithium aluminum hydride and di-isobutylaluminumhydride.

In another embodiment of the present invention, ketone used in step (a) is 3-pentanone.

In another embodiment of the present invention, yield and enantiomeric excess of β-amino alcohol is the range of 50%-75% and 90%-99% respectively.

In another embodiment of the present invention, β-amino alcohol of general formula 1A is preferably (S)—N-(5-chlorothiophene-2-sulfonyl)-β,β-diethylalaninol.

Some advantages of the present invention are:
1. Very short synthesis.
2. High yielding with high enantiomeric excess.
3. Use of cheap and easily available proline as organocatalysts.
4. Easy to use reagents.

DETAILED DESCRIPTION OF THE INVENTION

The present invention discloses preparation of chirally pure β-amino-alcohol intermediate (9) useful as intermediate for the synthesis of bioactive molecules via proline catalyzed alpha aminooxylation and alpha amination of carbonyl compound.

formula (9)

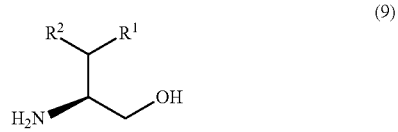

(9)

wherein, $R^1$ and $R^2$=ethyl, methyl, isopropyl or trifluoromethyl.

In an aspect, L-proline catalyzed α-aminooxylation and/or α-amination reactions of aldehyde (4) provide the key step for the introduction of chirality in achieving beta-amino-alcohol intermediate (9). The present invention also discloses enantioselective synthesis of N-sulfonyl β-amino alcohols of formula (1A) via L-proline catalyzed asymmetric α-amino oxylation and α-amination of aldehyde (4) in good yield and high enantioselectivity. The β-amino alcohol intermediate (9) is prepared from branched or unbranched ketone (1A) which on Horner-Wardworth-Emmons olefination (triethyl phosphonoacetate, NaH, THF) results in the corresponding α,β-unsaturated ester (2). The ester (2) on hydrogenation, reduction and subsequent oxidation gives an aldehyde (4) which on L-proline catalyzed α-aminooxylation and/or α-amination reactions results in amino alcohol (9) a key intermediate for the synthesis of N-sulfonyl β-amino alcohols. In a preferred aspect, the present invention provides preparation of β-amino alcohol intermediate (9) comprising α-amination of aldehyde using List's protocol to obtain protected amino alcohol, followed by hydrogenation of protected amino alcohol (10) with Raney nickel over hydrogen in presence of methanol and acetic acid.

Alternately, β-amino alcohol intermediate (9) is obtained via proline catalyzed α-aminooxylation of aldehyde (4) to obtain chiral diol (5), protecting stepwise the alcohol groups to obtain (7) followed by regiospecific azidation of (7) and reduction.

In an aspect, the β-amino alcohol intermediate (9) is converted to compound of Formula (1A) by reacting with furan sulfonyl halides to form chirally pure heterocyclic N-sulfonyl β-amino alcohols.

Thus in another preferred aspect, the present invention discloses preparation of the bioactive (S)—N-(5-chlorothiophene-2-sulfonyl)-β,β-diethyl alaninol. Accordingly, the intermediate β-amino alcohol intermediate (9) obtained via proline catalyzed α-amination and α-aminooxylation of aldehyde is condensed with 5-chlorothiophene-2-sulfonyl chloride in the presence of $Et_3N$ to obtain (S)—N-(5-chlorothiophene-2-sulfonyl)-β,β-diethyl alaninol.

As used herein, the term "chirally pure" refers to compounds which are at least 90 to 99% S-enantiomeric form as measured by chiral high performance liquid chromatography (HPLC).

The present invention relates to enantioselective synthesis of N-sulfonyl β-amino alcohols of formula (1A) via L-proline catalyzed asymmetric α-amino oxylation and α-amination of aldehyde (4) in good yield and high enantioselectivity.

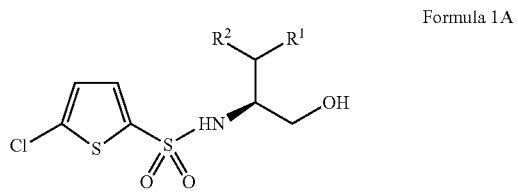

Formula 1A wherein, $R^1$ and $R^2$=ethyl, methyl, isopropyl or trifluoromethyl.

In an embodiment, proline catalyzed α-aminooxylation and α-amination reactions of aldehyde (4) constitute key steps for the introduction of chirality to obtain chirally pure β-amino alcohol intermediate (9). The general process for the preparation of β-amino alcohol intermediate (9) from aldehyde precursor (4) and its conversion to N-sulfonyl β-amino alcohols of formula (1) is given below in Scheme 1:

e. regioselective azidation of (7) with sodium azide in DMF at 60° C. to give TBS azide (8), and

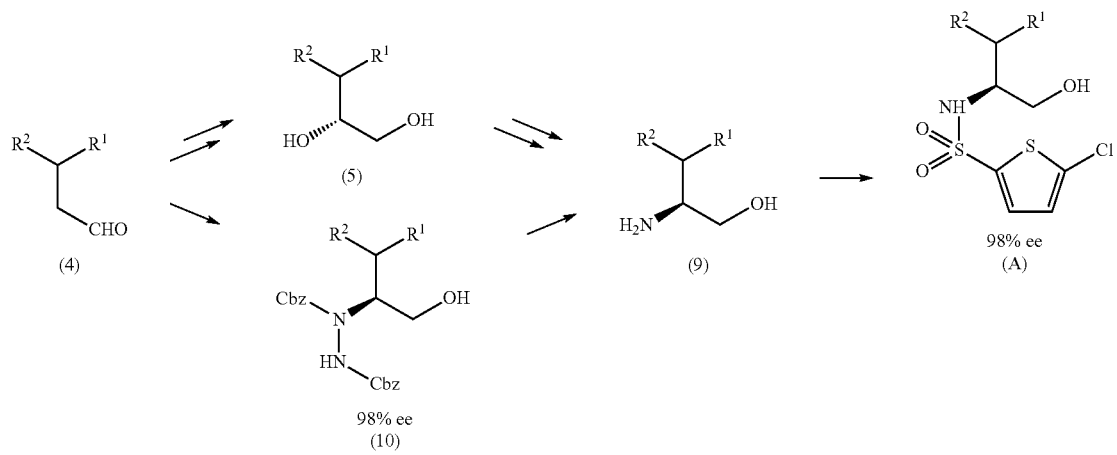

f. reduction of TBS azide with LiAlH$_4$ in THF to yield intermediate (9).

Hydrogenation of α,β-unsaturated ester (2) is performed using catalytic reduction with hydrogen gas in the presence of 10% palladium on carbon catalyst, or with metallic catalyst such as Raney nickel, rhodium, indium, Zn/HCl etc. The reduction of saturated ester to alcohol (3) is carried out in presence of NaBH$_4$, LiAlH$_4$, DIBAL etc. Hydrogenation and reduction can be carried out in presence of lower C1-C5 alcohols, dry THF, acetonitrile, DMF etc at ambient temperature.

In an embodiment, the process for the preparation of β-amino alcohol intermediate (9) and subsequently to compound of general Formula (1A) involves reaction of branched or unbranched ketone (1) such as acetone, diethylketone, ethyl methyl ketone, diphenyl ketone, acetophenone and the like as the starting compound which on Horner-Wardworth-Emmons olefination (triethyl phosphonoacetate, NaH, THF), gave the corresponding α,β-unsaturated ester (2). The ester (2) on further reactions yields the key precursor aldehyde (4) which on proline catalyzed α-aminooxylation and/or α-amination reactions results in β-amino alcohol intermediate (9).

Asymmetric α-amination of aldehydes using proline as the catalyst represents a burgeoning field of synthetic efforts toward synthesizing chiral building blocks, such as α-amino acids and β-amino-alcohols.

Accordingly, in a preferred embodiment, the process for the preparation of β-amino alcohol intermediate (9) comprises the steps of:

a. hydrogenation of α,β-unsaturated ester (2) and subsequent reduction to obtain saturated primary alcohol (3),
b. oxidation of alcohol (3) with IBX/DMSO to yield precursor aldehyde (4),
c. α-amination of aldehyde (4) using List's protocol to obtain protected amino alcohol (10), and
d. hydrogenation of (10) with Raney nickel over hydrogen (11.8 atm) in presence of methanol and acetic acid (5 drops) to yield (9).

Alternately, α-amino alcohol intermediate (9), an important intermediate in the synthesis of compound of formula (1A), can also be obtained by proline catalyzed α-aminooxylation of aldehyde (4).

The process for the preparation of β-amino alcohol intermediate (9) comprises the steps of:

a. hydrogenation of α,β-unsaturated ester (2) and subsequent reduction to obtain saturated primary alcohol (3),
b. oxidation of alcohol (3) with IBX/DMSO to yield precursor aldehyde (4).
c. α-aminooxylation of aldehyde (4) to obtain crude α-aminooxy alcohol and subsequent reduction with 10% Pd/C to furnish chiral diol (5),
d. selective protection of hydroxyl group in diol (5) to yield protected TBS ether (6) and further mesylation of TBS ether (6) to yield mesylate (7), The process for the preparation of β-amino alcohol intermediate (9) starting from branched or unbranched ketone (1) is given below in Scheme 2:

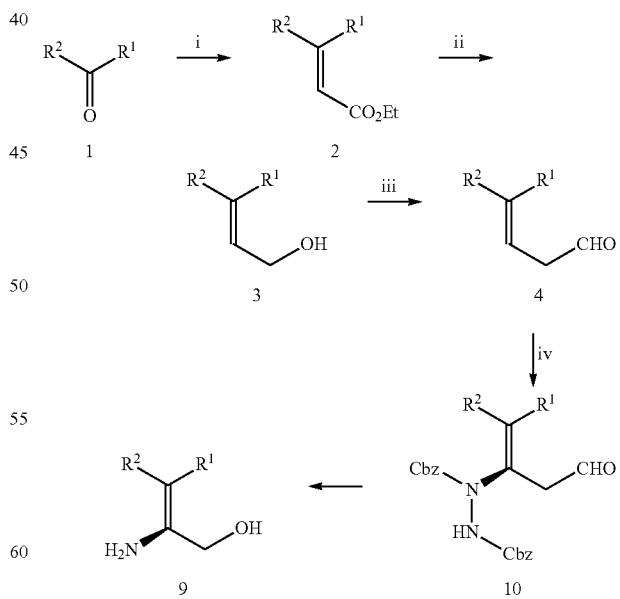

wherein R$^1$ and R$^2$=ethyl, methyl, isopropyl and trifluoromethyl.

The alternate process for the preparation of β-amino alcohol intermediate (9) is represented in Scheme 3:

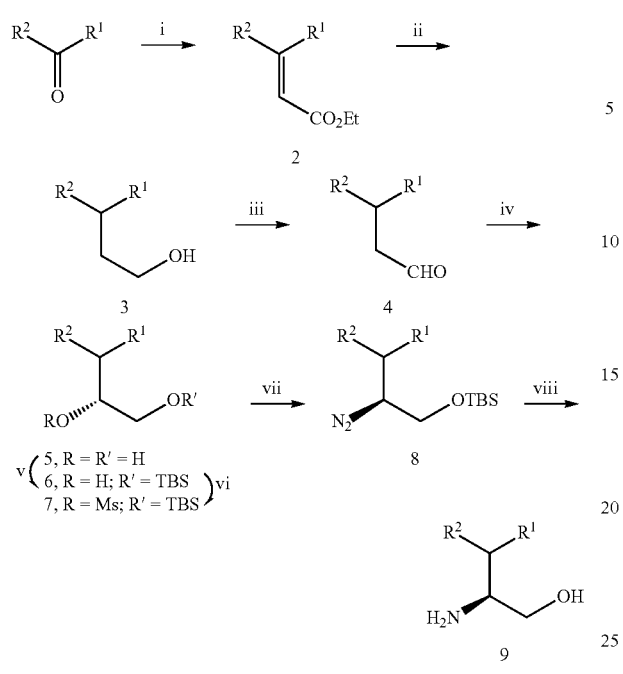

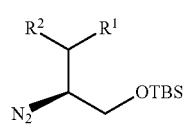

corresponding mesylate (7). The mesylation is carried out in presence of a base selected from triethylamine, pyridine, etc in presence of polar aprotic solvent methylene dichloride, DMF, THF, and acetonitrile etc. preferably methylene dichloride. However, attempts to purify the mesylate via column chromatography proved problematic due to its instability. The crude mesylate is therefore treated immediately with sodium azide in presence of ethyl acetate, DMF, THF, and acetonitrile etc. preferably THF at a temperature in the range of 55-70° C. to afford the corresponding azide (8). The azide (8) is then reduced using alkali metal hydrides such as NaBH$_4$, LiAlH$_4$, etc. in solvent such as ethyl acetate, DMF, THF, and acetonitrile etc, preferably THF at a temperature of 40-60° C. to give the key intermediate β-amino alcohol intermediate (9) which is accomplished with the simultaneous removal of TBS group (Scheme 3).

In an embodiment, the present invention discloses novel azide compound of formula (8):

wherein R$^1$ and R$^2$ is as defined above.

In an embodiment, referring to Scheme 2 and 3, α,β-unsaturated ester (2) is hydrogenated with Pd/C (10%) over 1-12 (1 atm) in lower alcoholic solvent such as methanol to produce crude saturated ester, which is directly subjected to reduction with LiAlH$_4$ in presence of dry THF, DMF, DMSO, acetonitrile etc preferably dry THF at 25° C. to yield saturated primary alcohol (3). This is followed by oxidation of primary alcohol (3) with IBX (o-iodoxy benzoic acid)/DMSO mixture to obtain the key precursor aldehyde (4).

The aldehyde (4) so formed is highly volatile, hence upon solvent extraction, it is immediately (without purification) subjected to proline-catalyzed α-aminooxylation and α-amination respectively.

In the preferred embodiment, as referred in Scheme 2, proline catalyzed α-amination of aldehyde (4) is carried out using List's protocol. Accordingly, aldehyde (4) is reacted with dibenzyl azo dicarboxylate in presence of D-proline (10 mol %) to produce the α-amino aldehyde, which upon in situ reduction with NaBH$_4$ afforded the protected amino alcohol (10). Compound (10) is then hydrogenated using Raney nickel in presence of methanol and acetic acid to compound (9).

In another embodiment, the L-proline-catalyzed α-aminooxylation of aldehyde (4) is carried out in a two-step reaction sequence as given below:

i. reacting aldehyde (4) with nitrosobenzene as the oxygen source in the presence of 20 mol % L-proline in CH3CN at −20° C. followed by its treatment with NaBH$_4$ in MeOH to give crude α-aminooxy alcohol in situ, and ii. subsequent reduction of the crude α-aminooxy alcohol with 10% Pd/C over 1 12 (1 atm) to obtain chiral diol (5).

The chiral diol (5) so formed is converted to novel azide compound of formula (8) and which is subsequently reduced to n-amino alcohol intermediate (9).

Selective protection of primary hydroxyl group in diol (5) is carried out using tert-Butyl dimethylsilyl chloride (TBSCl) in imidazole and CH2Cl2 to produce the TBS ether (6), followed by mesylation of the secondary alcohol to give the wherein, R$^1$ and R$^2$=ethyl, methyl, isopropyl or trifluoromethyl.

The organo catalyst L-proline used is 20 mole % which can be recycled and reused. Further, the β-amino alcohol may then be isolated using techniques known by those of skill in the art including but not limited to, chromatography and recrystallization. Recrystallization may be performed using a variety of organic and inorganic solvents known in the art to obtain chirally pure β-amino alcohol intermediate (9).

In yet another embodiment, chirally pure β-amino alcohol intermediate (9) is used for enantioselective synthesis of N-sulfonyl β-amino alcohols of formula (1A) by reacting with furan sulfonyl halides.

In another preferred embodiment, the present invention discloses enantioselective synthesis of (S)—N-(5-chlorothiophene-2-sulfonyl)-β,β-diethyl alaninol (wherein R$^1$ and R$^2$ are methyl) which comprises the steps of:

a. hydrogenation of α,β-unsaturated ester (2) and subsequent reduction to obtain saturated primary alcohol (3), b. oxidation of alcohol (3) with IBX (o-iodoxy benzoic acid)/DMSO to yield precursor aldehyde (4), c. α-amination of aldehyde (4) using List's protocol to obtain protected amino alcohol (10), and d. hydrogenation of (10) with Raney nickel over hydrogen (11.8 atm) in presence of methanol and acetic acid (5 drops) to yield (S)-2-amino 3ethyl pentan-1-ol (9) and further converting (9) to the desired product by a process known in the art.

Alternately, process for the enantioselective synthesis of (S)—N-(5-chlorothiophene-2-sulfonyl)-β,β-diethyl alaninol (wherein R$^1$ and R$^2$ are methyl) comprises the steps of:

a. hydrogenation of α,β-unsaturated ester (2) and subsequent reduction to obtain saturated primary alcohol (3), b. oxidation of alcohol (3) with IBX (o-iodoxy benzoic acid/DMSO to yield precursor aldehyde (4), c. α-aminooxylation of aldehyde (4) to obtain crude α-aminooxy alcohol and subsequent reduction with 10% Pd/C to furnish chiral diol (5),
d. selective protection of hydroxyl group in diol (5) to yield protected TBS ether (6) and further mesylation of TBS ether (6) to yield mesylate (7),
e. regioselective azidation of (7) with sodium azide in DMF at 60° C. to give TBS azide (8), and
f. reduction of TBS azide with LiAlH₄ in THF to yield (S)-2-amino 3ethyl pentan-1-ol (9) and further converting (9) to the desired product by a process known in the art.

Accordingly, the intermediate (S)-2-amino-3-ethyl pentan-1-ol (9) is condensed with 5-chlorothiophene-2-sulfonyl chloride in the presence of Et₃N to obtain (S)—N-(5-chlorothiophene-2-sulfonyl)-β,β-diethylalaninol, in 91% yield and 98% ee (determined by chiral HPLC).

Hydrogenation of α,β-unsaturated ester (2) is performed using catalytic reduction with hydrogen gas in the presence of 10% palladium on carbon catalyst, or with metallic catalyst such as Raney nickel, rhodium, indium, Zn/HCl etc. The reduction of saturated ester to alcohol (3) is carried out in presence of NaBH₄, LiAlH₄, DIBAL, etc. Hydrogenation and reduction can be carried out in presence of lower alcohols, dryTHF, acetonitrile, DMF etc at ambient temperature.

In an embodiment, the process for the enantioselective synthesis of (S)—N-(5-chlorothiophene-2-sulfonyl)-β,β-diethylalaninol, compound of formula (1A) is given in Schemes 4 and 5 below:

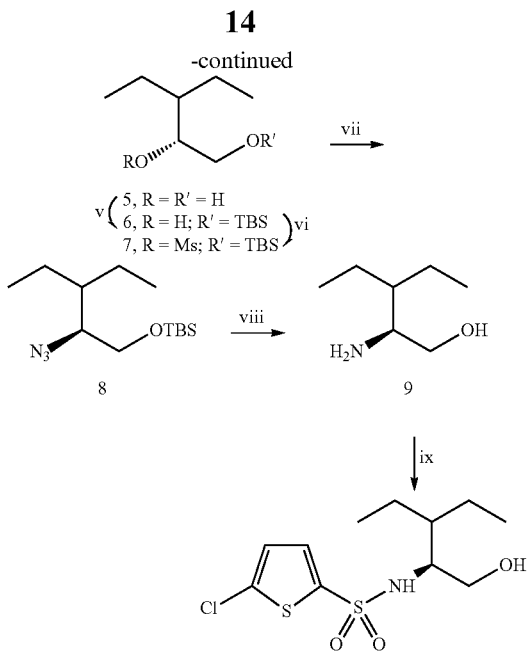

According to Scheme 4 and 5, α,β-unsaturated ester (2) is hydrogenated with Pd/C (10%) over H2 (1 atm) in lower alcoholic solvent such as methanol to produce crude saturated ester, which is directly subjected to reduction with LiAlH₄ in presence of dry THF, DMF, DMSO, acetonitrile etc preferably dry THF at 25° C. to yield saturated primary alcohol (3) in 83% yield. This is followed by oxidation of primary alcohol (3) with IBX (o-iodoxy benzoic acid)/DMSO mixture to obtain the key precursor aldehyde (4).

The aldehyde (4) so formed is highly volatile, hence upon solvent extraction, it is immediately (without purification) subjected to proline-catalyzed α-aminooxylation and α-amination respectively.

In the preferred embodiment, as referred to in Scheme 4, the process for the preparation of compound of Formula (1A) involves proline catalyzed αamination of aldehyde (4) using List's protocol. Accordingly, aldehyde (4) is reacted with dibenzyl azodicarboxylate in presence of D-proline (10 mol %) to produce the α-amino aldehyde, which upon in situ Scheme 4

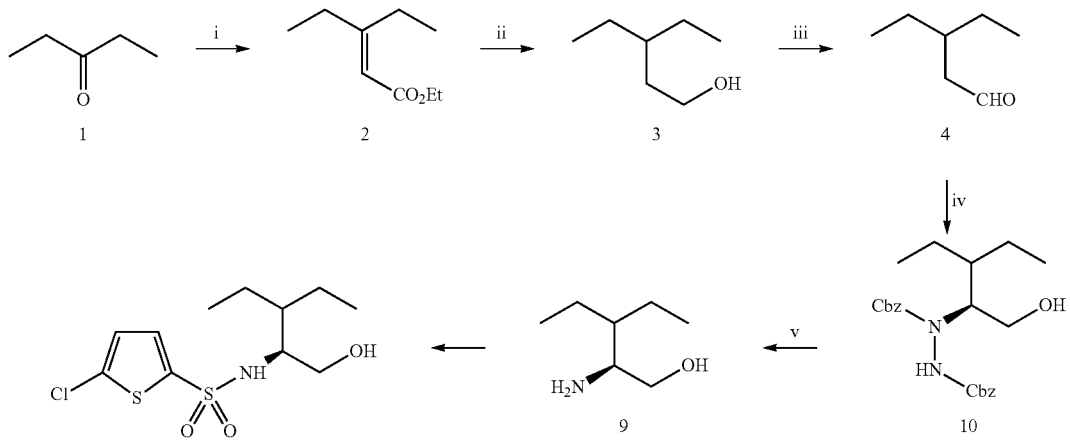

Scheme 5

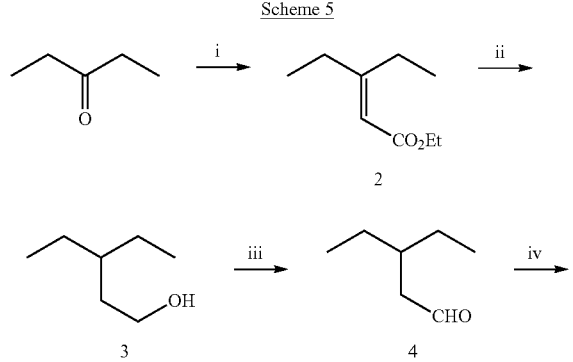

reduction with NaBH$_4$ afforded the protected amino alcohol (10) in 92% yield and 98% ee (determined by chiral HPLC). Compound (10) is then hydrogenated to compound (9) which is then condensed with 5-chlorothiophene-2-sulfonyl chloride in the presence of Et3N to obtain compound (1) in 91% yield and 98% ee (determined by chiral HPLC).

In alternate embodiment as disclosed in Scheme 5, the L-proline-catalyzed α-aminooxylation of aldehyde (4) is carried out in a two-step reaction sequence as given below:

i. reacting aldehyde (4) with nitrosobenzene as the oxygen source in the presence of 20 mol % L-proline in CH3CN at −20° C. followed by its treatment with NaBH$_4$ in MeOH to give crude α-aminooxy alcohol in situ, and ii. subsequent reduction of the crude α-aminooxy alcohol with 10% Pd/C over H2 (1 atm) to obtain chiral diol (5).

The chiral diol (5) is obtained in 77% yield and with 99% ee (determined from its Mosher ester analysis).

Accordingly, selective protection of primary hydroxyl group in diol (5) is carried out using tert-Butyl dimethylsilyl chloride (TBSCl) in imidazole and CH2Cl2 to produce the TBS ether (6) in 81% yield, followed by mesylation of the secondary alcohol to give the corresponding mesylate (7). The mesylation is carried out in presence of a base selected from triethylamine, pyridine, etc., in presence of polar aprotic solvent methylene dichloride, DMF, THF, and acetonitrile etc., preferably methylene dichloride. However, attempts to purify the mesylate via column chromatography proved problematic due to its instability. The crude mesylate is therefore treated immediately with sodium azide in presence of ethyl acetate, DMF, THF, and acetonitrile etc., preferably THF at a temperature in the range of 55-70° C. to afford the corresponding azide (8) in 78% yield {[α]D25 −21.3 (c 1.6, CHCl3)}. The azide (8) is then reduced using alkali metal hydrides such as NaBH$_4$, LiAlH$_4$ etc in solvent such as ethyl acetate, DMF, THF, and acetonitrile etc, preferably THF at a temperature of 40-60° C. to give the key intermediate β-amino alcohol intermediate (9) in 75% yield with 99% ee which is accomplished with the simultaneous removal of TBS group (Scheme 5).

In an embodiment, the organo catalyst L-proline used is 20 mole % which can be recycled and reused. Further, the β-amino alcohol may then be isolated using techniques known by those of skill in the art including but not limited to, chromatography and recrystallization. Recrystallization may be performed using a variety of organic and inorganic solvents known in the art.

In conclusion, the present invention provides a short synthetic route to preparation of bioactive of formula (1A) by incorporating a successful application of D-proline-catalyzed asymmetric α-amination of aldehyde (4) to give the corresponding amino alcohol intermediate (9) in 98% ee and with an overall yield of 45.2%. The operationally simple reactions with less number of steps, high overall yields requiring a relatively low amount of inexpensive and non-toxic proline as catalyst make this approach an attractive and useful process.

The following examples are given by way of illustration of the present invention and therefore should not be construed to limit the scope of the present invention.

EXAMPLES

Example 1

Preparation of (S)—N-(5-chlorothiophene-2-sulfonyl)-β,β-diethylalaninol (1A)

To a reaction vessel was added a mixture of 3-pentanone (6.4 g), triethyl phosphonoacetate (34 g), NaH (3.6 g), and enough dry THF (250 mL) at 0° C. and maintained for 8 h to obtain α,β-unsaturated ester (ethyl 3-ethylpent-2-enoate)(2) (93%). This was followed by passing hydrogen gas (1 atm) over 10% Pd/C (250 mg), in MeOH (100 mL), for about 12 h at 25° C. To the reaction mixture was further added LiAlH$_4$ (1.8 g), and dry THF (100 mL), at 0° C. for 12 h to obtain alcohol (3-ethylpentan-1-ol) (3) (83% for two steps). Alcohol (3) (6 g), was reacted with (o-iodoxy benzoic acid) (21.6 g), in dry DMSO (65 mL), at 25° C. for 2 h to yield aldehyde (3-ethylpentanal) (4). This is followed by addition of dibenzyl azodicarboxylate (6 g), D-proline (10 mol %) (820 mg), in presence of CH$_3$CN (250 mL), at 0-20° C. (stirring 2 h at 0° C. and 1 h at 20° C.) for 3 h followed by addition of NaBH$_4$ (7 g) in MeOH (100 mL) to obtain protected amino alcohol (S)-2-(1,2-Dibenzyloxycarbonylhydrazinyl)-3-ethylpentan-1-ol) (10) and then passing H2 gas (11.8 atm) over Raney Ni (200 mg), in MeOH (100 mL). AcOH 0.5 mL, (25° C., 24 h) to yield (S)-2-amino 3ethyl pentan-1-ol (9) (70%).

A mixture of (S)-2-amino 3ethyl pentan-1-ol (9) (200 mg) and methylene chloride (20 mL) was placed under argon, and cooled to 0° C. Triethyl amine (484 mg) was added followed by the drop wise addition of 5-chlorothiophene-2-sulfonyl chloride (347.2) in methylene chloride (5 mL) for 30 min to obtain (S)—N-(5-chlorothiophene-2-sulfonyl)-β,β-diethylalaninol (1A) (45.2% overall yield and 98% ee).

Example 2

Preparation of (S)—N-(5-chlorothiophene-2-sulfonyl)-β,β-diethylalaninol (1A)

To a reaction vessel was added a mixture of 3-pentanone (6.4 g), triethyl phosphonoacetate (34 g), NaH (3.6 g), and enough dry THF (250 mL), at 0° C. and maintained for 8 h to obtain α,β-unsaturated ester (ethyl 3-ethylpent-2-enoate) (2) (93%). This was followed by passing hydrogen gas (1 atm) over 10% Pd/C (250 mg), in MeOH (100 mL), for about 12 h at 25° C. To the reaction mixture was further added LiAlH$_4$ (1.8 g), and dry THF (100 mL), at 0° C. for 12 h to obtain alcohol (3-ethylpentan-1-ol) (3) (83% for two steps). Alcohol (3) (6 g), was reacted with (o-iodoxy benzoic acid) (21.6 g), in dry DMSO (65 mL), at 25° C. for 2 h to yield aldehyde (3-ethylpentanal) (4). This is followed by addition of PhNO (nitrosobenzene)(5 g), L-proline (20 mol %)(1.3 g), in acetonitrile (250 mL), at −20° C. for 24 h and then added NaBH$_4$ (7 g), in MeOH (100 mL). To the mixture is passed H2 gas (1 atm) over 10% Pd/C (250 mg), in MeOH (100 mL), for 12 h at 25° C., (77% over two steps) to obtain diol (3-ethylpentane-1,2-diol) (5). Then tert-butyl silylchloride (TBSCl) (7.5 g), in imidazole (4.5 g), and methylene chloride (200 mL), is added to the diol (5) at 0-25° C. (addition at 0° C. stirring at 25° C.) for 2 h to obtain (3-ethyl-2-hydroxy-pent-1-yloxy(tert-butyl) dimethylsilane) (6) (81%) followed by treatment with mesyl chloride (7.7 g), in triethyl amine (20 mL), for 45 min to yield (7). To the protected diol (3-ethyl-2-methansolphonyl-pent-1-yloxy(tert-butyl)dimethylsilane) (7) was added NaN$_3$ (4 g), in dry DMF (100 mL), at 60° C. for 30 h, (78% for two steps) to obtain compound (2-azido-3-ethylpentyloxy tet-butyl dimethylsilane) (8). To the compound (8) was added LiAlH$_4$ (2 g), in dry THF (100 mL), at 50° C. for 12 h to afford (S)-2-amino 3ethyl pentan-1-ol (9)(75%). A mixture of (S)-2-amino 3ethyl pentan-1-ol (9) (200 mg) and methylene chloride (20 mL) was placed under argon, and cooled to 0° C. Triethyl amine (484 mg) was added followed by the drop wise addition of 5-chlorothiophene-2-sulfonyl chloride (347.2) in methylene chloride (5 mL) for 30 min to obtain (S)—N-(5-chlorothiophene-2-sulfonyl)-β,β-diethylalaninol (1A) (45.2% overall yield and 98% ee).

Spectral Data:
1. ((S)-2-azido-3-ethylpentyloxy)(tert-butyl)dimethylsilane (8): [α]D25 −21.3 (c 1.6, CHCl3); IR (CHCl3, cm-1): 3064, 2896, 2110, 1600 1496, 1454, 1255, 1217, 967, 837: 1H NMR (200 MHz, CDCl3) δ 0.08 (s, 6H), 0.84-0.92 (m, 15H), 1.33-1.37 (m, 5H), 3.40-3.45 (m, 1H), 3.64-3.77 (m, 2H); 13C NMR (50 MHz, CDCl3): δ −5.6, 11.2, 11.3, 18.2, 21.8, 22.5, 25.8, 41.8, 65.0, 66.2; Anal. Calcd for C13H29N3OSi requires C, 57.52; H, 10.77; N, 15.48. found C, 57.67; H, 10.83; N, 15.45%.
2. (S)-2-(1,2-Dibenzyloxycarbonylhydrazinyl)-3-ethyl-pentan-1-ol (10): Colorless crystalline solid; m.p. 121° C. (crystallized from ethanol); [α]D25 +20.0 (c 1.0, CHCl3): 98% ee HPLC analysis: Column: ODH, mobile phase: hexane/isopropyl alcohol (9/1), flaw rate: 0.5 mL/min, retention time: 12.59 min (−)-isomer, 15.59 min (+)-isomer. IR (CHCl3, cm-1): 3510, 3258, 2959, 2878, 1721, 1681, 1537, 1455, 1380, 1267; $^1$H NMR (200 MHz, CDCl3) δ 0.69-0.87 (m, 6H), 1.26-1.43 (m, 5H), 3.38-3.80 (m, 2H), 4.14-4.22 (m, 1H), 4.33 (br. s, 1H), 5.12-5.27 (m, 4H), 6.39 (br. s, 1H), 7.26-7.36 (m, 10H); 13C NMR (50 MHz, CDCl3): δ 9.8, 10.1, 20.5, 21.3, 38.9, 60.4, 62.9, 68.2, 68.5, 127.8, 128.1, 128.3, 128.4, 128.5, 128.6, 135.1, 135.7, 157.3; Anal. Calcd for C23H30N2O5 requires C, 66.65; H, 7.30; N, 6.76. found C, 66.53; H, 7.10; N, 6.89%.
3. (S)—N-(5-chlorothiophene-2-sulfonyl)-β,β-diethyla-laninol (1A): Colorless crystalline solid: m.p. 115-117° C. (crystallized from heptane:ethylacetate 4:1) {lit.5b m.p. 115-117.6° C.}; [α]D25 +10.3 (c 0.3, MeOH) {lit.5b [α]D25 +10.81 (1% solution, MeOH)}; 98% ee HPLC analysis: Column: ODH, mobile phase: hexane/isopropyl alcohol (9/1), flow rate: 0.5 mL/min: retention time: 13.01 min (+)-isomer, 13.56 min (−)-isomer). IR (CHCl3, cm-1): 3519, 3301, 3068, 3034, 2957, 2881, 1615, 1456, 1337, 1130, 1090; $^1$H NMR (200 MHz, CDCl3) δ 0.77-0.87 (m, 6H), 1.18-1.34 (m, 5H), 1.93 (br, s, 1H), 3.31-3.42 (m, 1H), 3.57-3.60 (m, 2H), 4.93 (br, s, 1H), 6.92 (d, J=4.0 Hz, 1H), 7.42 (d, J=4.0 Hz, 1H): 13C NMR (50 MHz, CDCl3): δ 11.4, 11.6, 22.7, 21.9, 42.8, 57.7, 62.6, 126.5, 131.5, 137.2, 140.1; Anal. Calcd for C11H18ClNO3S2 requires C, 42.37; H, 5.82; N, 4.49. found C, 42.26; H, 5.76; N, 4.50%.

What is claimed is:
1. A process for the preparation of chirally pure β-amino alcohol of general formula 1A

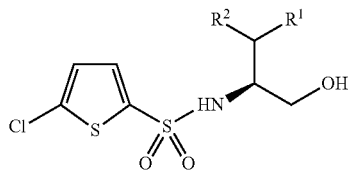

General formula 1A wherein $R^1$ and $R^2$=ethyl, methyl, isopropyl or trifluoromethyl, comprising the steps of:
a) adding a ketone, triethyl phosphonoacetate, NaH and THF at temperature ranging between −10° C. to 10° C. for a period ranging between 5-15 h to obtain α,β-unsaturated ester;
b) hydrogenating α, the β-unsaturated ester as obtained in step (a) with H$_2$ gas and in the presence of a catalyst for a period ranging between 12 h to 24 h at temperature ranging between 15° C. to 35° C. to obtain saturated primary alcohol;
c) oxidising the alcohol as obtained in step (b) with IBX (o-iodoxy benzoic acid) in DMSO for a period ranging between 1 h to 4 h at temperature ranging between 10° C. to 35° C. to obtain aldehyde;
d) α-aminating the aldehyde as obtained in step (c) using List's protocol for a period ranging between 2 h to 8 h at temperature ranging between −10° C. to 10° C. to obtain protected amino alcohol;
e) hydrogenating the protected amino alcohol as obtained in step (d) with Raney nickel over hydrogen in presence of methanol and acetic acid for a period ranging between 22 h to 48 h at temperature ranging between 15° C. to 35° C. to yield intermediate alcohol; and
f) condensing the intermediate alcohol as obtained in step (e) with 5-chlorothiophene-2-sulfonyl chloride in the presence of triethylamine for a period ranging between 30 min to 6 h at temperature ranging between −10° C. to 15° C. to yield β-amino alcohol of general formula 1A.

2. The process of claim 1, wherein catalyst used in step (b) is 10% Pd/C, lithium aluminum hydride, sodiumborohydride or rhodium catalyst.

3. The process of claim 1, wherein ketone used in step (a) is 3-pentanone.

4. The process of claim 1, wherein yield and enantiomeric excess of β-amino alcohol is in the range of 50%-75% and 90%-99%, respectively.

5. A process for the preparation of chirally pure β-amino alcohol, wherein the said process comprises the step of:

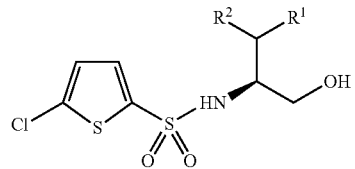

General formula 1A wherein, $R^1$ and $R^2$=ethyl, methyl, isopropyl or trifluoromethyl
a) adding a ketone, triethyl phosphonoacetate, NaH and THF at temperature ranging between −10° C. to 10° C. for a period ranging between 5-15 h to obtain α,β-unsaturated ester;
b) hydrogenating the α,β-unsaturated ester as obtained in step (a) with H$_2$ gas and in the presence of a catalyst for a period ranging between 12 h to 24 h at temperature ranging between 15° C. to 35° C. to obtain saturated primary alcohol;
c) oxidising the alcohol as obtained in step (b) with IBX (o-iodoxy benzoic acid) in DMSO for a period ranging between 1 h to 4 h at temperature ranging between 10° C. to 35° C. to obtain aldehyde;
d) α-aminooxylating the aldehyde as obtained in step (c) in the presence of L-proline and PhNO (nitroso benzene) at temperature ranging between −30° C. to 0° C. for a period ranging between 15 h to 30 h to obtain crude α-aminooxy alcohol and subsequent reduction with H$_2$ gas and a catalyst at temperature ranging between 15° C. to 35° C. for a period ranging between 12 h to 35 h to furnish chiral diol;

e) protecting hydroxyl group in the diol as obtained in step (d) with tert-Butyl dimethylsilyl chloride (TBSCl) in imidazole and $CH_2Cl_2$ to yield protected ether and further mesylation of protected ether to yield protected mesylate;
f) regioselective azidation of the protected mesylate as obtained in step (e) with sodium azide in DMF at temperature ranging between 45° C. to 70° C. for a period ranging between 20 h to 48 h to give protected azide;
g) reduction of the protected azide as obtained in step (f) with $LiAlH_4$ in THF at temperature ranging between 40° C. to 60° C. for a period ranging between 5 h to 20 h to yield the intermediate alcohol;
h) condensating the intermediate alcohol as obtained in step (g) with 5-chlorothiophene-2-sulfonyl chloride in the presence of Et3N to yield β-amino alcohol of general formula 1A.

6. The process of claim 5, wherein catalyst used in step (b) is 10% palladium on carbon catalyst, Raney nickel, rhodium, indium, Zn/HCl, sodium borohydride, lithium aluminum hydride or di-isobutylaluminumhydride.

7. The process of claim 5, wherein ketone used in step (a) is 3-pentanone.

8. The process of claim 5, wherein yield and enantiomeric excess of β-amino alcohol is in the range of 50%-75% and 90%-99%, respectively.

9. The process of claim 1, wherein β-amino alcohol of general formula 1A is (S)—N-(5-chlorothiophene-2-sulfonyl)-β,β-diethylalaninol.

10. The process of claim 5, wherein β-amino alcohol of general formula 1A is (S)—N-(5-chlorothiophene-2-sulfonyl)-β,β-diethylalaninol.

* * * * *